United States Patent [19]

Casperson et al.

[11] Patent Number: 5,376,146
[45] Date of Patent: Dec. 27, 1994

[54] TWO-PART AQUEOUS COMPOSITION FOR COLORING HAIR, WHICH FORMS A GEL ON MIXING OF THE TWO PARTS

[75] Inventors: Steve Casperson, Milford, Conn.; Stanley Pohl, Scarsdale, N.Y.; Michael Wong, Easton, Conn.

[73] Assignee: Bristol-Myers Squibb Company, New York, N.Y.

[21] Appl. No.: 112,162

[22] Filed: Aug. 26, 1993

[51] Int. Cl.$^5$ ............................................. A61K 7/13
[52] U.S. Cl. .......................................... 8/408; 8/405; 8/406; 8/410; 8/412; 8/435; 8/557; 8/558; 8/606; 8/913
[58] Field of Search ................... 8/405, 406, 557, 606, 8/408, 435, 410, 412, 558, 913

[56] References Cited

U.S. PATENT DOCUMENTS

| | | | |
|---|---|---|---|
| 3,930,792 | 1/1976 | Alperin et al. | 8/606 |
| 4,532,127 | 7/1985 | Feinland et al. | 8/406 |
| 4,566,875 | 1/1986 | Grollier et al. | 8/406 |
| 4,776,855 | 10/1988 | Pohl et al. | 8/406 |
| 4,927,627 | 5/1990 | Schrader et al. | 8/406 |
| 5,102,655 | 4/1992 | Yoshihara et al. | 8/406 |

Primary Examiner—Paul Lieberman
Assistant Examiner—Caroline L. Dusheck
Attorney, Agent, or Firm—Anthony M. Santini

[57] ABSTRACT

A two part aqueous composition for coloring human hair which forms a gel on mixing of an alkaline aqueous lotion first part having a pH of from about 7 to about 11 containing from about 0.005% by weight to about 5% by weight of at least one primary intermediate and at least one coupler for the formation of oxidation dyes, from about 0.1% to about 5% of a monomeric quaternary ammonium compound having one long chain alkyl substituent, from about 0.5% to about 15% by weight of an amphoteric surfactant and at least 70% by weight water, and an aqueous developer second part having a pH of from about 2 to about 6 containing from about 0.5% by weight to about 40% by weight of a peroxide oxidizer and from about 0.1% by weight to about 20% by weight of a water insoluble anionic polymer which dissolves in the formed gel.

15 Claims, No Drawings

TWO-PART AQUEOUS COMPOSITION FOR COLORING HAIR, WHICH FORMS A GEL ON MIXING OF THE TWO PARTS

RELATED APPLICATION

Copending and commonly owned U.S. patent application Ser. No. 08/112,161 describes and claims compositions somewhat similar to those of this invention.

FIELD OF THE INVENTION

This invention relates to oxidative, aqueous, hair coloring compositions.

BACKGROUND OF THE INVENTION

When oxidation dyes of the type comprising primary intermediates and couplers are used in the dyeing of human hair, the procedure usually involves the use of a two part system. One part is the lotion formulation which contains a variety of ingredients, including the oxidation dye precursors, and forms a gel immediately prior to application to the human hair, when mixed with the second part, the developer formulation containing a suitable oxidizing agent. The developer usually contains an oxidizing agent, such as hydrogen peroxide and as a consequence some of the natural melanin pigment of the hair may be initially destroyed. The precursors in the lotion penetrate into the hair and are oxidized to produce the desired color. Such systems will generally contain 50% or more of organic solvents and surfactants, and require relatively high levels of dye precursors to produce the desired color.

several conditions are important for the procedures using oxidative dyes to work properly. These include:
1. The formulations must be stable to insure a reasonable shelf life.
2. The compositions formed by mixing the lotion and developer must have theological properties whereby application, either by use of a brush or with the fingers, can readily distribute the dye throughout the hair mass and yet in the absence of stress, dripping or running from the hair during the color development period can be substantially avoided.
3. The dye mixture, as applied to the hair, should allow rapid diffusion of the dye precursors from the dye mixture into the hair fiber.
4. The mixture, while thick enough to stay in place during the color development period should be readily rinseable from the hair with water.
5. The mixture should preferably contain conditioning agents which leave the hair in a condition such that it is easy to detangle while wet and also feel smooth and be readily managed when dry.
6. The lotion and developer should preferably, but not necessarily, have comparable viscosities in order to facilitate mixing.
7. The dyeing effect should be rapid, with a dyeing time preferably under thirty minutes.

In conventional permanent hair dye products, the reological properties have generally been attained by the use of a dye lotion containing a high level of surfactants and organic solvents to provide a thin lotion which, on mixture with a highly aqueous developer solution of the oxidizing agent forms a dye mixture with the desired gel-like consistency. The disadvantage of this approach is that the dye mixture still contains a high level of surfactants which tend to retard the diffusion of the dye precursors into the hair. The preferred surfactants in commercial products have been nonionic or anionic materials which do not provide any conditioning. The preferred conditioners for human hair are cationic surfactants which provide excellent conditioning but are incompatible with anionic surfactants.

There have been many efforts to produce oxidative hair dyeing compositions having the desired properties, listed above, while at the same time avoiding the aforesaid problems.

U.S. Pat. Nos. 3,303,213; 3,331,781; 3,436,167 and 3,891,385 describe the use in hair treating compositions of specific amphoteric surfactants such as the sodium salt of N-($N^1$, $N^1$-dimethyl-aminopropyl)-$N^2$-alkyl (fatty) asparagine wherein the "fatty" moiety is derived from the fatty acids of tallow. According to the patents, the amphoteric surfactant can be employed with organic solvents and any of a variety of cationic, anionic or non-ionic surface active agents. There is no indication of the use of quaternary ammonium salts in the compositions.

U.S. Pat. No. 4,402,700 describes hair dyeing compositions containing quaternary ammonium compounds and also cites the possible uses of amphoteric surfactants in the compositions. These compositions, however, require the uses of organic solvents and nonionic surfactants, and the amount of water in the compositions is less than 50%.

U.S. Pat. No. 4,532,127 describes hair coloring compositions containing oxidative dyes together with an oxidizing agent. The compositions require the presence of quaternary amine compounds containing two long chain alkyl radicals each having about 10 to 26 carbon atoms. Any of a variety of surfactants may be present in the composition which, although they have a high water content may contain organic solvents. The lotions of the patent contain di-long chain alkyl quaternary ammonium compounds in the presence of relatively large amounts of non-ionic surfactants. They are said to be superior to a comparison lotion containing a mono-long chain alkyl quaternary ammonium compound in combination with an amphoteric surfactant. The lotions of this patent suffer from the disadvantage of having high levels of surfactant thus inhibiting rapid diffusion of the dye precursors into the hair. Furthermore, di-long chain alkyl quaternary ammonium are poorly biodegradable, particularly as compared to the mono-long chain alkyl quaternary ammonium compounds. The compositions disclosed are free of anionic surfactants and anionic polymers.

U.S. Pat. No. 4,663,158 describes hair conditioning compositions containing an amphoteric surfactant together with at least one quaternary cationic polymer such as poly (methacrylamidopropyl)trimethy ammonium chloride sold under the trade name Clairquat-1. The compositions are acidic.

U.S. Pat. No. 4,563,188 discloses hair dyeing compositions containing specific para-phenylenediamine derivatives which may contain any of several types of surfactants as well as organic solvents.

U.S. Pat. No. 5,137,538 describes oxidative hair dyeing compositions containing specific para phenylenediamines and N,$N^1$ diphenylalkylenediamines. The compositions may be acidic or alkaline. They may contain organic solvents and anionic, cationic, non-ionic or amphoteric surfactants.

It is known to thicken hair lotion/developer mixtures by the use of water soluble polyacrylic acid polymers such as those known under the CTFA dictionary names polyacrylic acid or carbomer. When these thickeners are incorporated in the alkaline dye lotion they produce a thick cream or gel which is difficult to mix with the aqueous hydrogen peroxide solution. Furthermore, it has been observed that these water soluble polymers are not stable in aqueous hydrogen peroxide solutions.

U.S. Reissue Pat. No. 33786 teaches that rapid dyeing with highly aqueous compositions can be achieved through the use of a certain acrylate copolymer viz an acrylate/steareth-20 methacrylate copolymer in the developer. Such polymers produce a thickening effect only when the developer is added to the alkaline lotion containing the color precursor. The disadvantage of the use of acrylate copolymers, or any other anionic polymer, is that they tend to deactivate quaternary ammonium conditioning compounds by complexation. Furthermore, products containing a simple aqueous acrylate system are difficult to rinse from the hair. Additionally, experience has shown that lotions and developers containing the specific anionic copolymer of U.S. Re. Pat. No. 33786 are difficult to formulate in that the viscosity of the resulting mixture is not readily controllable.

It is an object of this invention to provide stable hair dyeing compositions which avoid the aforesaid problems while at the same time providing rapid dyeing permanent hair coloring systems having excellent rheological properties. The compositions of the invention are readily rinseable from the hair at the completion of the color development stage and leave the hair in excellent condition.

It is a further object of the invention to provide lotions and developers which can be readily formed into a gelled mixture having an appropriate viscosity to remain on the hair for a sufficient period to achieve the desired hair coloring effect.

It is yet another object of this invention to provide a two part composition which may be free of organic solvents and contain substantially lower amounts of surfactants than has generally been heretofore employed.

BRIEF SUMMARY OF THE INVENTION

This invention comprises a two part system comprising aqueous, oxidative, hair coloring compositions (lotions and developers) for mixture with each other shortly before use to form a gel. The lotion comprises an aqueous alkaline composition having a pH of from about 7 to 11 and a water content of at least about 70% by weight, a tinctorily effective amount of oxidative dye precursors, an amphoteric surfactant and at least one monomeric quaternary ammonium cationic surfactant having one long chain alkyl substituent containing from about 10 to 26 carbon atoms. The second part, i.e. the developer is an aqueous composition with a pH of from about 2 to about 6, preferably 2.5 to 4.5. It contains a peroxide oxidizing agent and at least one substantially water insoluble anionic acrylic polymer which is solubilized on admixture of the lotion and developer.

DETAILED DESCRIPTION OF THE INVENTION

The components in the aqueous first part of the compositions of this invention, i.e. the lotion, include water, the oxidizable dye precursors, an amphoteric surfactant and a monomeric quaternary ammonium cationic surfactant having one long chain alkyl substituent.

The water content of the composition is at least about 70% weight and may be as high as 95% or higher.

Unless otherwise specified the amounts of the various ingredients in the compositions of this invention are in percent by weight based on the total weight.

Amphoteric surfactants belong to the category of surface active chemicals that possess a positive and a negative charge in the same molecule and behave as a cation or an anion depending on the pH of the medium. In general, the positive charge is located on a nitrogen atom while the negative charge is carried by a carboxyl or sulfonate group. There are a large number of amphoteric surfactants that are suitable for use in this invention. They include, for example, the asparagine derivatives identified in the first three patents mentioned above as well as a variety of well known betaines, sultaines, glycinates and propionates which may be represented by the following structural formulas:

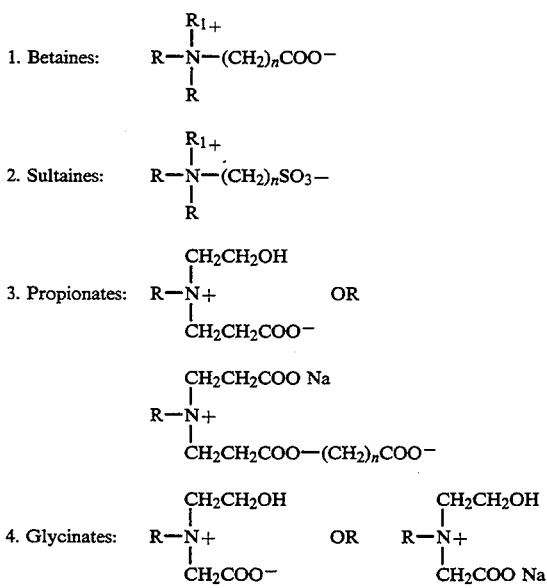

In the formulas, R is an alkyl or alkylamido group containing from about 10 to about 20 carbon atoms, R, $R_2$ and $R_3$ are alkyl or hydroxyalkyl groups, which may be the same or different, and contain up to about five carbon atoms and n is a positive integer up to about five.

Typical amphoteric surfactants that are suitable for use in this invention include:
Lauryl betaine, lauroamphoglycinate, lauroamphopropylsulfonate, lauroamphopropionate, lauroamphocarboxyglycinate, lauryl sultane, myristamidopropyl betaine, myristyl betaine, myristamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, cocoamphopropylsulfonate.

The selection of the amphoteric surfactant or mixture of surfactants for use in this invention is not critical. They may be selected from amongst those suggested above, or from any of a number of other known amphoteric surfactants. The amount of amphoteric surfactant in the compositions is normally from about 0.5% to about 15% by weight preferably 2% to 8% by weight.

The amphoteric surfactants presently preferred for use in this invention are:
Cocamidopropyl betaine, coco-betaine, stearyl betaine, cocoamphocarboxyglycinate, cocoamphodipropionate, and stearoamphoglycinate.

The pH of the lotions of this invention will generally be from about 7 to about 11. It is preferred, however, that this pH be in the range of 7.5 to 9.5.

Any of a wide variety of alkaline reagents can be used to adjust the pH of the hair coloring compositions. Ammonium hydroxide, because of its freedom from toxicity over a wide concentration range and its economy, is an acceptable alkalizing agent. However, there can be used in place of, or together with, ammonium hydroxide any other compatible ammonia derivative as an alkalizing agent, such as an alkylamine, for example ethylamine, or triethylamine; or alkanolamines, for example ethanolamine, diethanolamine, aminomethyl propanol, aminomethyl propanediol and trishydroxymethyl aminomethane. Likewise, any other of the organic or inorganic alkalizing agents may be used, such as sodium or potassium hydroxide, sodium or potassium carbonate, sodium phosphate, sodium hydrogen phosphate, sodium silicate, guanidine hydroxide and the like. The preferred alkaline reagents are ammonium hydroxide, sodium carbonate and ethanolamine.

With the reagents listed above, the selected pH will generally be achieved if the lotion contains from about 0.1% to 5% by weight of alkaline reagent.

The oxidative dye precursors employed in the practice of this invention comprise one or more primary intermediates together with one or more couplers. The selection of specific intermediates or couplers determines the ultimate color of the treated hair. Such selection is not a critical aspect of the practice of the invention.

A wide variety of primary intermediates can be employed in this invention including, for example:
paraphenylenediamines, corresponding to the formula:

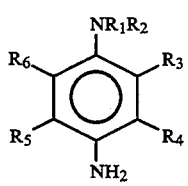

in which $R_1$ and $R_2$, which may be identical or different, can denote hydrogen, a $C_1$–$C_6$ lower alkyl group, a $C_1$–$C_6$ alkyl radical substituted with one or more hydroxy group(s) or with a methoxy, methylsulphonylamino or aminocarbonyl group, a furfuryl group, or a phenyl radical optionally substituted with an amino group, $R_3$ and $R_6$ denote, independently of one another, hydrogen, a $C_1$–$C_6$ lower alkoxy group, a halogen atom such as a chlorine atom, a $C_1$–$C_6$ lower alkyl group, or a $C_1$–$C_6$ lower alkyl group substituted with one or more hydroxy group(s), and $R_4$ and $R_5$ denote, independently of one another, hydrogen, a $C_1$–$C_6$ lower alkoxy group, a $C_1$–$C_6$ lower alkyl group, or a halogen atom such as chlorine, as well as their salts with inorganic or organic acids; N,N'-diphenylalkylenediamines in which the phenyl groups are substituted at the para position with an OH or amino group optionally substituted with a $C_1$–$C_6$ alkyl group, it being possible for the amino groups joined by the alkylene group to be substituted with $C_1$–$C_6$ alkyl, $C_1$–$C_6$ hydroxyalkyl or $C_1$–$C_6$ aminoalkyl; para-aminophenols; ortho-aminophenols; orthophenylenediamines, and heterocyclic oxidation bases.

Among the useful compounds of the formula shown above, there may be mentioned p-phenylenediamine, 2-methylparaphenylenediamine, 2-methoxy-paraphenylenediamine, 2-chloro-N-methyl-paraphenylenediamine, N-furfuryl-para-phenylenediamine, 3-methoxy-$N^1$-methyl-paraphenylenediamine, 2-chloro-paraphenylenediamine, N-methyl-para-phenylenediamine, 2,3-dimethyl-para-phenylenediamine, 5-chloro-$N^1$-methyl-p-phenylenediamine, 5-methyl-$N^1,N^1$-dimethyl-p-phenylenediamine, 5-methyl-$N^1$-ethyl-$N^1$-(amino-carbonyl-methyl)-p-phenylenediamine, 5-methyl-$N^1$-ethyl-$N^1$-ethylsulphonylaminoethyl)-p-phenylenediamine, N-(2-methoxy-ethyl)-p-phenylenediamine, 2,6-dimethyl-p-phenylenediamine, N,N-bis(2-hydroxyethyl)-p-phenylenediamine. The N,$N^1$-diphenylalkylenediamines include, for example, N,$N^1$-bis-(2-hydroxyethyl)-N,$N^1$-bis(p-aminophenyl)ethylenediamine. Their salts with acids such as the monohydrochlorides dihydrochlorides or sulphates are also suitable.

Among p-aminophenols which are usable according to the invention, there may be mentioned p-aminophenol, 2-methyl-p-aminophenol, 3-methyl-p-aminophenol, 2,3-dimethyl-p-aminophenol, 2,6-dimethyl-p-aminophenol, 3-methoxy-p-aminophenol, 2-chloro-p-aminophenol, N-methyl-p-aminophenol and 3-(methylthio)-p-aminophenol, of which p-aminophenol is preferred.

Among ortho bases, ortho-aminophenol, 5-chloro-orthoaminophenol and ortho-phenylenediamine are chosen more especially according to the invention.

Among heterocyclic bases, it is preferable, according to the invention, to use 2,3-diamino-6-methoxy-pyridine and 2-(2-hydroxyethyl)amino-5-aminopyridine and their salts, and still more especially 3,6-diaminopyridine, 2,6-dimethoxy-3-aminopyridine, 2-methylamino-3-amino-6-methoxypyridine, 2,5-diaminopyridine, 2-(N-hydroxyethyl)amino-5-amino pyridine, and 2-(N,N-bishydroxyethyl)amino-5-aminopyridine.

More especially preferred primary intermediates are p-phenylenediamine 2-methyl-p-phenylenedamine, N-(2-methoxyethyl)-p-phenylenediamine, N,N-bis(2-hydroxyethyl)-p-phenylenediamine and p-aminophenol.

Among couplers or color modifiers there may be mentioned, in particular, the compounds corresponding to the formula:

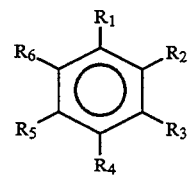

in which $R_1$ denotes hydroxy or an amino group which can be substituted with one or more $C_1$–$C_6$ hydroxyalkyl groups; $R_3$ and $R_5$, independently of one another, can denote hydrogen, a hydroxy group, an amino group optionally substituted with a $C_1$–$C_6$ lower hydroxyalkyl group or a $C_1$–$C_6$ lower alkyl group; and $R_2$, $R_4$ and $R_6$ can denote a hydrogen atom or a $C_1$–$C_6$ alkoxy group, a hydroxyalkoxy group or a $C_1$–$C_6$ lower alkyl group; it also being possible for $R_3$ and $R_4$ together to form a methylenedioxy group.

Among the suitable couplers, there may be mentioned 2-methoxy-5-aminophenol, 2-methoxy-5-[N-(2-hydroxyethyl)amino]phenyl, 1,3-diamino-2,6-dimethoxybenzene, 2-methoxy-1-(N-methylamino)-4-(2-hydroxyethoxy)-3-aminobenzene, 1,3-diamino-6-methoxybenzene, 1,3-diamio-4,6-dimethoxybenzene, 4,6-dimethoxy-1,3-bis[N-(2-hydroxyethyl)-amino]benzene, 2,6-dimethoxy-3-[N-(2-hydroxyethyl)amino]-1-aminobenzene, 2,6-dimethyoxy-3-[N-(2-hydroxyethyl)amino]-1-aminobenzene, 2,4 dimethoxy-3-[N-(2-hydroxyethyl)amino]-phenol, 1,3-bis[N-(2-hydroxyethyl)amino]-4-methoxybenzene, 3-amino-4-methoxyphenol, 3,4-methylenedioxy-1-aminobenzene, 2,6-dimethyl-3-[N-(2-hydroxy-ethyl)amino]phenol, 2,6-dimethyl-3-aminophenol, 4-ethoxy-1-amino-3-[N,N-bis(2-hydroxyethyl)amino]benzene, (2,4-diaminophenoxy)ethanol, (2-amino-N-methyl-4-aminophenoxy)-ethanol, 1-methoxy-2-[N-(2-hydroxyethyl)amino]-4-aminobenzene, 3,4-methylenedioxy-6-methoxyphenol, 3-amino-6-methylphenol, 3,4-methylenedioxy-6-methoxyaminobenzene, 3-aminophenol, 1,3-dihydroxybenzene-4-(hydroxyethoxy)-1,3-phenylenediamine, 4,6-(dihydroxyethoxy)-1,3-phenylenediamine, and 1,3-phenylenediamine.

Other suitable couplers are 6-aminobenzomorpholine, 1-amino-7-naphthol, 6-hydroxybenzomorpholine, 1-naphthol, 1,3-dihydroxynaphthalene and 1,2-dihydroxy-benzene. Among heterocyclic couplers there may be mentioned 2,6-dihydroxypyridine, 2,6-diaminopyridine, 2-amino-4-hydroxypyrindine, 2-hyroxy-4-amino-pyridine, 2-hydroxy-5-aminopyridine, 2-amino-6-hydroxypyridine and the like. Included also are further derivatives of 2,6-diamino alkyl pyridines where the amino nitrogen of one or both amino groups is mon- or distributed with a $C_1$–$C_6$ alkyl group such as the methyl, propyl, isopropyl, butyl, iso or sec-butyl, pentyl, sec-pentyl neopoentyl, t-butyl, hexyl, 3-methyl pentyl or 4-methylpentyl groups. The amino groups of either the amino-4-hyroxy- or 2-hydroxy-4-amino-pyridines may also have mon- or d-$C_1$–$C_6$ alkylation on the nitrogen atoms.

The 2,6 amino-, or 4-amino-2-hydroxy- or 2-amino-4-hydroxy pyridine nitrogens may also either singly or doubly be derivatized with alkoxy substituents of carbon lengths of 1 to 6 with specific mention of 2-hydroxyethyl, 3-hydroxypropyl, 4-hydroxybutyl, 5-hydroxypentyl, 6-hydroxyhexyl, 2-hydroxypropyl, 2-hydroxybutyl, 2-hydroxypentyl, 2-hydroxyhexyl, 3-hydroxybutyl, 3-hydroxypentyl, 2-hydroxyhexyl, 4-hydroxypentyl and 5-hydroxypentyl groups.

Among trihydroxylated derivatives of benzene, there may be mentioned 1,2,4-trihydroxybenzene, 1,2,4-trihydroxy-5-alkylbenzenes in which the alkyl group is a $C_1$–$C_6$ lower alkyl group and 1,2,3-trihydroxybenzene, and their salts.

Among diaminohydroxybenzenes, there may be mentioned 2,4-diaminophenol and 2,5-diamino-4-methoxy-1-hydroxybenzene, and their salts.

Among aminodihyroxybenzenes, there may be mentioned 2-amino-1,4-dihydroxybenzene, 1,4-dihydroxy-4-diethylaminobenzene and 4-aminoresorcinol, and their salts.

Among substituted 1,2-dihydroxybenzenes, 4-methyl-1,2-dihydroxybenzene and 3-methoxy-1,2-dihydroxybenzene are especially preferred.

The aminohydroxybenzenes are chosen, in particular, from 2- amino-4-methoxyphenol, 2-aminophenol, 4,6-dimethoxy-3-amino-hydroxybenzene and 2,6-dimethyl-4-[N-(p-hydroxyphenyl)amino]-1-hydroxybenzene, and their salts.

By way of a triaminobenzene, there may be mentioned 1,5-diamino-2-methyl-4-[N-(p-hydroxyphenyl)amino]-benzene and its salts.

Also suitable as a coupler is N-acetyl dopa.

The table below lists some of the preferred primary intermediates and couplers for use in this invention.

| Preferred Primary Intermediates and Couplers | |
|---|---|
| Primary Intermediates: | p-phenylenediamine |
| | p-aminophenol |
| | o-aminophenol |
| | N,N-bis(2-hydroxyethyl)-p-phenylenediamine |
| | 2,5-diaminopyridine |
| | p-toluenediamine |
| Couplers: | resorcinol |
| | 1-naphthol |
| | 5-amino-o-cresol |
| | 2-methylresorcinol |
| | N-acetyl dopa |
| | 4,6-di(hydroxyethoxy)-m-phenylenediamine |
| | m-phenylenediamine |

The primary intermediate(s) and coupler(s) in the aqueous lotion of the invention will normally be employed in equimolar quantities, each at a concentration of about 0.0005% to about 5% by weight, preferably 0.005% to 2.5% by weight.

The quaternary ammonium salt employed in the lotion part of the composition may be selected from any of a number of known monomeric salts including those of the formula

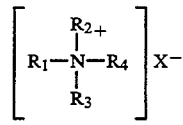

wherein $R_1$, $R_2$ and $R_3$, which may be the same or different, represent benzyl or lower alkyl groups containing 1 to 6 carbon atoms, $R_4$ represents a long chain alkyl group containing from about 12 to about 22 carbon atoms and X is an anion, normally a halide, preferably a chloride. Typical representatives of this class of compounds include cetyltrimethylammonium bromide and chloride, benzyldocosyldimethylammonium chloride (behenalkonium chloride), N,N,N-trimethyl-1-docosanammonium chloride (behentrimonium chloride), cetyl dimethylbenzylammonium chloride (cetalkonium chloride) and stearyl trimethylammonium chloride (steartrimonium chloride), all of which are known compounds.

The monomeric quaternary ammonium compounds employed in the lotions of this invention function not only as surfactants, but also as hair conditioners since under the conditions employed for hair coloring they tend to neutralize the anionic charge normally present on the keratin of human hair. The compounds thus make two important contributions to the conditioning of the hair. One is that they neutralize the anionic charge on the keratin. Another is that the presence of the long chain alkyl group improves the lubricity of the hair. The conditioned hair is easy to detangle while wet. It will feel smooth and be readily managed when dry.

Specific quaternary ammonium compounds suitable for use in this invention are: cetyltrimethylammonium chloride, cetethyldimonium bromide, cetrimonium tosylate, behenalkonium chloride, behentrimonium chloride, cetalkonium chloride, stearalkonium chloride, steartrimonium chloride, dodecyldimethylehtylbenzyl ammonium chloride, myristalkonium chloride, and myristalkonium bromide.

Presently preferred quaternary ammonium compounds for use in this invention are: behentrimonium chloride, cetrimonium chloride and stearalkonium chloride.

The concentration of the quaternary ammonium compound in the lotion of this invention is from about 0.1% to about 5.0% by weight, preferably 0.5% to 2.0% by weight.

The viscosity of the completely formulated lotion of the invention when it is ready to mix with the developer is from about 1 cps to about 5000 cps, preferably 1 cps to 500 cps.

The lotion may contain organic solvents to assist in dissolving the dye precursors. However, it has been observed that in the compositions of this invention, the organic solvent content should be kept at a minimum. More solvent than is necessary to dissolve the precursors may have the effect of retarding diffusion of the precursors into the hair for reaction. Accordingly, the organic solvent content of the lotion may be from 0% by weight to about 5% by weight.

Typically useful solvents include alcohols containing up to three carbon atoms such as ethanol and isopropanol, polyhydroxy alcohols such as propylene or hexylene glycol and lower alkyl ethers thereof such as ethoxy ethers.

Other conventional agents often employed in hair coloring compositions may be employed in the lotion or in the developer. These include, for example, fragrances, coloring agents and chelating agents. Antioxidants such as sodium sulfite erythroboric acid and ascorbic acid may also be included to inhibit premature oxidating.

The oxidizing composition or developer employed in the invention is an acidic aqueous composition which comprises the selected oxidizing agent together with one or mere anionic polymers which are insoluble in water.

The preferred oxidizing agent for use in the developer of the invention is hydrogen peroxide although other peroxides may be employed. These include, for example, urea peroxide, melamine peroxide, perborates and percarbonates such as sodium perborate or percarbonate. The concentration of peroxide in the developer may be from about 0.5% to about 40% by weight, preferably 0.5% to 30% by weight. If the preferred hydrogen peroxide is employed, the concentration will be from about 0.5% to about 12% by weight, preferably 3% to 9% by weight.

An important aspect of the practice of this invention is the selection of the anionic polymer for use in the developer. As indicated above, some anionic polymers including certain acrylate polymers tend to deactivate quaternary ammonium compounds by forming complexes.

There are however, certain anionic polymers: which are insoluble in water, stable to peroxide and do not complex with and precipitate the quaternary ammonium compounds used herein. They are readily identified by a few simple tests as will be readily apparent to the skilled artisan. Suitable anionic polymers include copolymers formed from acrylic acid, and methacrylic acid lower alkyl esters of these acids as well as copolymers which include acrylamide or methacrylamide. The preferred polymers for use in the developer are esters of acrylic polymers and polyalkylene glycol ethers of long chain fatty alcohols, for example esters of acrylic polymers and polyethylene glycol ethers of stearyl alcohol such as steareth-20 represented by the formula $CH_3(CH_2)_{16}CH_2(OCH_2CH_2)_nOH$ wherein n has an average value of 20.

Anionic polymers which include homologs of stearyl alcohol such as cetyl and arachadyl alcohol or mixtures of such alcohol segments such as ceteath-20 which is based on a mixture of cetyl and stearyl alcohols may be used.

The presently preferred anionic polymers are alkali soluble polymers available from Rohm and Haas, Philadelphia, Pa. under the trade marks Aculyn 22 and Aculyn 33. The former is believed to be a steareth-20 ester of a copolymer formed from acrylic or methacrylic acid or their lower alkyl esters. These preferred copolymers may be employed separately or together in any selected proportion.

The concentration of anionic polymer in the developer is from about 0.1% by weight to about 20% by weight, preferably 0.5% to 10% by weight.

The developer may also contain from 0 to about 0.2% by weight of a stabilizer such as phanacetin or ethylene diamine tetracetic acid (EDTA).

The viscosity of the developer as prepared for mixture with the lotion is from about 1 cps to about 5000 cps by weight, preferably 1 cps to 500 cps by weight.

It is desirable but not essential that the viscosities of the lotion and the developer be close to each other. If the difference in viscosities is too great they will be difficult to mix. On shaking the thinner solution will agitate well, but the thicker component will be more difficult to agitate and the rate of blending will be slowed down.

The pH of the developer is from about 2 to about 6, preferably 2.5 to 4.5. Any of a variety of non-toxic acids or buffers may be employed to maintain pH. Phosphoric acid is the most preferred.

The lotion and developer are mixed just before application to the hair. On the hair, they form a stable gel with enough consistency and body to remain on the hair during the complete coloring period without dripping or running. The primary intermediate and coupler, i.e. the dye precursors diffuse rapidly into the hair together with the oxidizing agent. The dyes form within the hair fiber and, since they are large molecules, remain in the hair so that the color change is permanent. The term "permanent" means that the dye does not readily wash out of the hair with ordinary shampoos. The color achieved with the products of this invention is so stable that it may survive as many as 20 shampoos without noticeable change.

At the end of the coloring period, the composition is washed from the hair with an ordinary water rinse followed by a shampoo.

The compositions of this invention may be separately provided in a kit or package form ready for mixing by the user, either professional or personal, to initiate the dyeing process. It is possible to combine the lotion and the developer by mixing them directly on the hair of the user. If they are mixed on the hair, it is preferable to add the lotion first. It is preferred to mix them in a mixing vessel for subsequent application to the hair as the gel forms.

The kit provided in accordance with this invention comprises those containers. In the most convenient form, there will be two containers, one containing the lotion, the other the developer. It may also be convenient to package the developer in separate containers one with the oxidizing agent, the other with the anionic polymer in water. With both embodiments of the invention, the ingredients in the aqueous composition of the first container will include the dye precursors, the amphoteric surfactant, the quaternary ammonium compound and the alkaline reagent all in the amounts defined above.

The method of the invention comprises applying the mixture to the hair to be colored and allowing it to remain in contact with the hair until the desired hair color has been attained after which the composition is removed from the hair as described above.

The following non-limiting examples are given by way of illustration only.

EXAMPLES 1–40

The lotions and developers shown below are prepared by mixing the separate components. When these 8 lotions are separately mixed with any of the 5 developers, 40 different gelled hair coloring compositions are prepared which color human hair when applied thereto and thoroughly incorporated in the hair by finger manipulation.

by weight to about 5% by weight of at least one primary intermediate and at least one coupler for the formation of oxidation dyes, from about 0.1% to about 5% of a monomeric quaternary ammonium compound of the formula

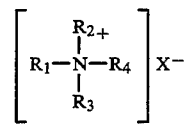

wherein $R_1$, $R_2$ and $R_3$, which may be the same or different, represent benzyl or lower alkyl groups containing 1 to 6 carbon atoms, $R_4$ represents a long chain alkyl group containing from about 12 to about 22 carbon atoms and X is an anion, from about 0.5% to about 15% by weight of an amphoteric surfactant and at least 70% by weight water; and b: an aqueous developer having a pH of from about 2 to about 6 containing from about 0.5% by weight to about 40% by weight of a peroxide oxidizer and from about 0.1% by weight to about 20% by weight of a water insoluble anionic polymer which dissolves to form said gel when mixed with said alkaline aqueous lotion.

2. A composition as in claim 1 wherein:
a: the pH of the lotion is from 7.5 to 9.5, the primary intermediate and coupler content is from 0.005% to 2.5% by weight, the content of quaternary ammonium compound is from 0.5% to 2.0% by weight, the amphoteric surfactant content is from 2% to 8% by weight and the water content is at least 70% by weight; and
b: the pH of the aqueous developer is from 2.5 to 4.5,

| Ingredients | LOTIONS | | | | | | | |
|---|---|---|---|---|---|---|---|---|
| | 1 | 2 | 3 | 4 | 5 | 6 | 7 | 8 |
| Cocamidopropyl betaine | 4.5 | 4.5 | — | — | — | 6.0 | 6.0 | — |
| Cocamphocarboxyglycinate | — | — | 5.0 | 5.0 | — | — | — | 2.0 |
| Cocoamphydipropionate | — | — | — | — | 3.0 | — | — | — |
| Ammonium hydroxide | 1.0 | 1.0 | — | — | — | 0.5 | 0.3 | — |
| Sodium carbonate | — | — | 1.2 | — | — | — | — | — |
| Sodium bicarbonate | — | — | 0.5 | — | — | — | — | — |
| Sodium citrate | — | — | 0.4 | — | — | — | — | — |
| Aminomethyl propanol | — | — | — | 3.0 | — | — | — | — |
| Monoethanol amine | — | — | — | — | 5.0 | — | — | — |
| Behentrimonium chloride | 1.0 | — | — | 2.0 | 0.5 | 3.0 | — | — |
| Cetrimonium chloride | — | 2.0 | — | — | — | — | — | 1.0 |
| Stearalkonium chloride | — | — | 2.0 | — | — | — | 5.0 | — |
| P-phenylenediamine | 0.2 | 0.3 | 0.5 | 0.4 | 0.1 | 1.0 | 3.0 | 0.5 |
| Resorcinol | 0.1 | 0.1 | 0.2 | 0.1 | 0.1 | 0.3 | 1.0 | 0.2 |
| EDTA | 0.1 | 0.1 | 0.1 | 0.1 | 0.1 | 0.1 | 0.1 | 0.1 |
| Sodium sulfite | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 |
| Water | 92.9 | 91.8 | 89.9 | 89.2 | 91.0 | 88.9 | 84.4 | 96.0 |

| Ingredients | Developers | | | | |
|---|---|---|---|---|---|
| | 1 | 2 | 3 | 4 | 5 |
| Hydrogen peroxide | 3.0 | 6.0 | 6.0 | 3.0 | 6.0 |
| Aculyn 33 | 1.5 | 1.5 | 2.5 | 1.0 | 5.0 |
| Aculyn 22 | 1.5 | 1.5 | 1.5 | 5.0 | 5.0 |
| EDTA | 0.1 | 0.1 | 0.1 | 0.1 | 0.1 |
| Phosphoric acid | 0.1 | 0.1 | 0.1 | 0.1 | 0.1 |
| Water | 93.8 | 90.8 | 89.8 | 90.8 | 83.8 |

What is claimed is:

1. A two part aqueous composition for coloring human hair which forms a gel on mixing of the two parts comprising:
a: an alkaline aqueous lotion having a pH of from about 7 to about 11 containing from about 0.005% the peroxide oxidizer content is from 0.5% to 30% by weight and the anionic polymer content is 0.5% to 10% by weight.

3. A composition as in claim 1 wherein the developer contains from about 0.5% to about 12% by weight of hydrogen peroxide.

4. A composition as in claim 2 wherein the developer contains from about 0.5% to about 12% by weight of hydrogen peroxide.

5. A kit containing a two part aqueous composition which forms a gel on mixing of the two parts for coloring human hair comprising separate first and second containers:
  a: the first container containing an alkaline aqueous lotion having a pH of from about 7 to about 11 containing from about 0.005% by weight to about 5% by weight of at least one primary intermediate and at least one coupler for the formation of oxidation dyes, from about 0.1% to about 5% by weight of a monomeric quaternary ammonium compound of the formula

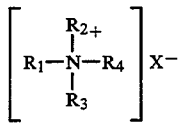

wherein $R_1$, $R_2$ and $R_3$, which may be the same or different, represent benzyl or lower alkyl groups containing 1 to 6 carbon atoms, $R_4$ represents a long chain alkyl group containing from about 12 to about 22 carbon atoms and X is an anion from about 0.5 to about 15% by weight of an amphoteric surfactant and at least 70% by weight water;
  b: the second container containing an aqueous developer having a pH of from about 2 to about 6 containing from about 0.5% by weight to about 40% by weight of a peroxide oxidizer and from about 0.1% by weight to about 20% by weight of a water insoluble anionic polymer which dissolves to form said gel when mixed with said alkaline aqueous lotion.

6. A kit as in claim 5 wherein:
  a: the pH of the lotion is from 7.5 to 9.5, the primary intermediate and coupler content is from 0.005% to 2.5% by weight, the content of quaternary ammonium compound is from 0.5% to 2.0% by weight, the amphoteric surfactant content is from 2% to 8% by weight and the water content is at least 70% by weight; and
  b: the pH of the aqueous developer is from 2.5 to 4.5, the peroxide oxidizer content is from 0.5% to 30% by weight and the anionic polymer content is 0.5% to 10% by weight.

7. A kit as in claim 5 wherein the developer contains from about 0.5% to about 12% by weight of hydrogen peroxide.

8. A kit as in claim 6 wherein the developer contains from about 0.5% to about 12% by weight of hydrogen peroxide.

9. A method of coloring human hair which comprises contacting the hair with a mixture of a two part aqueous composition which forms a gel on mixing of the two parts comprising:
  a: an alkaline aqueous lotion having a pH of from about 7 to about 11 containing from about 0.005% by weight to about 5% by weight of at least one primary intermediate and at least one coupler for the formation of oxidation dyes, from about 0.1% to about 5% of a monomeric quaternary ammonium compound of the formula

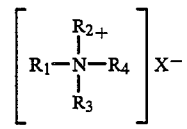

wherein $R_1$, $R_2$ and $R_3$, which may be the same or different, represent benzyl or lower alkyl groups containing 1 to 6 carbon atoms, $R_4$ represents a long chain alkyl group containing from about 12 to about 22 carbon atoms and X is an anion, from about 0.5% to about 15% by weight of an amphoteric surfactant and at least 70% by weight water;
  b: an aqueous developer having a pH of from about 2 to about 6 containing from about 0.5% by weight to about 40% by weight of a peroxide oxidizer and from about 0.1% by weight to about 20% by weight of a water insoluble anionic polymer which dissolves to form said gel when mixed with said alkaline aqueous lotion, and maintaining such contact until the hair is permanently colored.

10. A method as in claim 9 wherein:
  a: the pH of the lotion is from 7.5 to 9.5, the primary intermediate and coupler content is from 0.005% to 2.5% by weight, the content of quaternary ammonium compound is from 0.5% to 2.0% by weight, the amphoteric surfactant content is from 2% to 8% by weight and the water content is at least 70% by weight; and
  b: the pH of the aqueous developer is from 2.5 to 4.5, the peroxide oxidizer content is from 0.5% to 30% by weight and the anionic polymer content is 0.5% to 10% by weight.

11. A method as in claim 9 wherein the developer contains from about 0.5% to about 12% by weight of hydrogen peroxide.

12. A method as in claim 10 wherein the developer contains from about 0.5% to about 12% by weight of hydrogen peroxide.

13. A composition as in claim 1 wherein the amphoteric surfactant is selected from the group consisting of lauryl betaine, lauroamphoglycinate, lauroamphopropylsulfonate, lauroamphopropionate, lauroamphocarboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, and cocoamphopropylsulfonate; and
  wherein the primary intermediate is selected from the group consisting of paraphenylenediamines corresponding to the following formula:

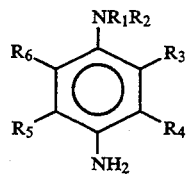

in which $R_1$ and $R_2$ denote hydrogen, a $C_1$–$C_6$ lower alkyl group, a $C_1$–$C_6$ alkyl radical substituted with at least one hydroxy group or with a methoxy, methylsulphonylamino or aminocarbonyl group, a furfuryl group, or a phenyl radical optionally substituted with an amino group, $R_3$ and $R_6$ denote, independently of one another, hydrogen, a $C_1$–$C_6$ lower alkoxy group, a halogen atom, a $C_1$–$C_6$ lower alkyl group, or a $C_1$–$C_6$ lower alkyl group substituted with at least one hydroxy group, and $R_4$ and $R_5$ denote, independently of one another, hydrogen, a $C_1$–$C_6$ lower alkyl group, or a halogen atom, their salts with inorganic or organic acids;

N,N'-diphenylalklenediamines in which the phenyl groups are substituted at the para position with an OH or amino group optionally substituted with a $C_1$–$C_6$ alkyl group; para-aminophenols; ortho-aminophenols; ortho-phenylenediamines; and heterocyclic oxidation bases; and wherein the coupler is selected from the group consisting of 1-naphthol and compounds corresponding to the following formula:

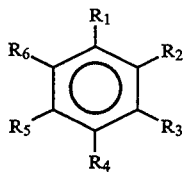

in which $R_1$ denotes hydroxy or an amino group optionally substituted with at least one $C_1$–$C_6$ hydroxyalkyl group, $R_3$ and $R_5$, independently of one another, denote hydrogen, a hydroxy group, an amino group optionally substituted with a $C_1$–$C_6$ lower hydroxyalkyl group or a $C_1$–$C_6$ lower alkyl group, and $R_2$, $R_4$ and $R_6$ denote a hydrogen atom or a $C_1$–$C_6$ alkoxy group, a hydroxyalkoxy group or a $C_1$–$C_6$ lower alkyl group;

wherein the quaternary ammonium salt is selected from salts corresponding to the formula:

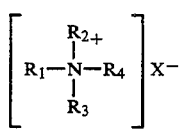

wherein $R_1$, $R_2$ and $R_3$ represent benzyl or lower alkyl groups containing 1 to 6 carbon atoms, $R_4$ represents a linear long chain alkyl group containing from about 12 to about 22 carbon atoms and X is an anion; and wherein the anionic polymer is selected from copolymers formed from acrylic acid, methacrylic acid and its lower alkyl esters, acrylamide and methacrylamide.

14. A kit as in claim 5 wherein the amphoteric surfactant is selected from the group consisting of lauryl betaine, lauroamphoglycinate, lauroamphopropylsulfonate, lauroamphopropionate, lauroamphocarboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoaphocarboxyglycinate, coco-betaine, cocoamphopropionate, and cocoamphopropylsulfonate; and wherein the primary intermediate is selected from the group consisting of paraphenylenediamines corresponding to the following formula:

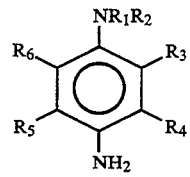

in which $R_1$ and $R_2$ denote hydrogen, a $C_1$–$C_6$ alkyl radical substituted with at least one hydroxy group or with a methoxy, methylsulphonylamino or aminocarbonyl group, a furfuryl group, or a phenyl radical optionally substituted with an amino group, $R_3$ and $R_6$ denote, independently of one another, hydrogen, a $C_1$–$C_6$ lower alkoxy group, a halogen atom, a $C_1$–$C_6$ lower alkyl group, or a $C_1$–$C_6$ lower alkyl group substituted with at least one hydroxy group, and $R_4$ and $R_5$ denote, independently of one another, hydrogen, a $C_1$–$C_6$ lower alkoxy group, a $C_1$–$C_6$ lower alkyl group, or a halogen atom, their salts with inorganic or organic acids;

N,N'-diphenylalkylenediamines in which the phenyl groups are substituted at the para position with an OH or amino group optionally substituted with a $C_1$–$C_6$ alkyl group; para-aminophenols; ortho-aminophenols; ortho-phenylenediamines; and heterocyclic oxidation bases; and wherein the coupler is selected from the group consisting of 1-naphthol and compounds corresponding to the following formula:

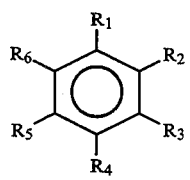

in which $R_1$ denotes hydroxy or an amino group optionally substituted with at least one $C_1$–$C_6$ hydroxyalkyl group, $R_3$ and $R_5$, independently of one another, denote hydrogen, a hydroxy group, an amino group optionally substituted with a $C_1$–$C_6$ lower hydroxyalkyl group or a $C_1$–$C_6$ lower alkyl group, and $R_2$, $R_4$ and $R_6$ denote a hydrogen atom or a $C_1$–$C_6$ alkoxy group, a hydroxyalkoxy group or a $C_1$–$C_6$ lower alkyl group; and wherein the quaternary ammonium salt is selected from salts corresponding to the formula:

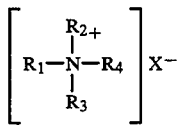

wherein $R_1$, $R_2$ and $R_3$ represent benzyl or lower alkyl groups containing 1 to 6 carbon atoms, $R_4$ represents a linear long chain alkyl group containing from about 12 to about 22 carbon atoms and X is an anion; and wherein the anionic polymer is selected from copolymers formed from acrylic acid, methacrylic acid and its lower alkyl esters, acrylamide and methacrylamide.

15. A method as in claim 9 wherein the amphoteric surfactant is selected from the group consisting of lauryl betaine, lauroamphoglycinate, lauroamphopropylsulfonate, lauroamphopropionate, lauroamphocarboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoaphocarboxyglycinate, cocobetaine, cocoamphopropionate, and cocoamphopropylsulfonate; and wherein the primary intermediate is selected from the group consisting of paraphenylenediamines corresponding to the following formula:

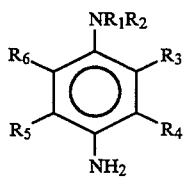

in which $R_1$ and $R_2$ denote hydrogen, a $C_1$–$C_6$ alkyl radical substituted with at least one hydroxy group or with a methoxy, methylsulphonylamino or aminocarbonyl group, a furfuryl group, or a phenyl radical optionally substituted with an amino group, $R_3$ and $R_6$ denote, independently of one another, hydrogen, a $C_1$–$C_6$ lower alkoxy group, a halogen atom, a $C_1$–$C_6$ lower alkyl group, or a $C_1$–$C_6$ lower alkyl group substituted with at least one hydroxy group, and $R_4$ and $R_5$ denote, independently of one another, hydrogen, a $C_1$–$C_6$ lower alkoxy group, a $C_1$–$C_6$ lower alkyl group, or a halogen atom, salts with inorganic or organic acids;

N,N'-diphenylalkylenediamines in which the phenyl groups are substituted at the para position with an OH or amino group optionally substituted with a $C_1$–$C_6$ alkyl group; para-aminophenols; ortho-aminophenols; ortho-phenylenediamines; and heterocyclic oxidation bases; and wherein the coupler is selected from the group consisting of 1-naphthol and compounds corresponding to the following formula:

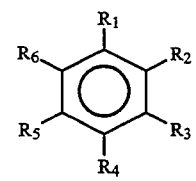

in which $R_1$ denotes hydroxy or an amino group optionally substituted with at least one $C_1$–$C_6$ hydroxyalkyl group, $R_3$ and $R_5$, independently of one another, denote hydrogen, a hydroxy group, an amino group optionally substituted with a $C_1$–$C_6$ lower hydroxyalkyl group or a $C_1$–$C_6$ lower alkyl group, and $R_2$, $R_4$ and $R_6$ denote a hydrogen atom or a $C_1$–$C_6$ alkoxy group, a hydroxyalkoxy group or a $C_1$–$C_6$ lower alkyl group; and wherein the quaternary ammonium salt is selected from salts corresponding to the formula:

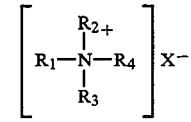

wherein $R_1$, $R_2$ and $R_3$ represent benzyl or lower alkyl groups containing 1 to 6 carbon atoms, $R_4$ represents a linear long chain alkyl group containing from about 12 to about 22 carbon atoms and X is an anion; and wherein the anionic polymer is selected from copolymers formed from acrylic acid, methacrylic acid and its lower alkyl esters, acrylamide and methacrylamide.

* * * * *

UNITED STATES PATENT AND TRADEMARK OFFICE
CERTIFICATE OF CORRECTION

PATENT NO. : 5,376,146
DATED : December 27, 1994
INVENTOR(S) : Casperson et al.

It is certified that error appears in the above-identified patent and that said Letters Patent is hereby corrected as shown below:

Title page, item [73], please change

"Bristol-Myers Squibb Company, New York, N.Y."

to --Clairol, Inc., New York, N.Y.--.

Signed and Sealed this

Fifth Day of September, 1995

Attest:

BRUCE LEHMAN

Attesting Officer

Commissioner of Patents and Trademarks